United States Patent
Tojo et al.

(10) Patent No.: US 7,850,993 B2
(45) Date of Patent: Dec. 14, 2010

(54) DRUG-RELEASING SYSTEM OF BIODEGRADABLE POLYMER TYPE

(75) Inventors: Kakuji Tojo, Fukuoka (JP); Yoshiko Fujikawa, Setagaya-Ku (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 708 days.

(21) Appl. No.: 10/468,585

(22) PCT Filed: Feb. 21, 2002

(86) PCT No.: PCT/JP02/01577

§ 371 (c)(1),
(2), (4) Date: Aug. 20, 2003

(87) PCT Pub. No.: WO02/67993

PCT Pub. Date: Jun. 9, 2002

(65) Prior Publication Data

US 2004/0076676 A1     Apr. 22, 2004

(30) Foreign Application Priority Data

Feb. 27, 2001   (JP) ............................... 2001-53035

(51) Int. Cl.
*A61K 9/14*   (2006.01)
(52) U.S. Cl. .................................... 424/486
(58) Field of Classification Search ........................ None
See application file for complete search history.

(56) References Cited

U.S. PATENT DOCUMENTS 4,645,664 A * 2/1987 Lange ..................... 514/772.7
5,248,700 A * 9/1993 Lance ..................... 514/772.3

FOREIGN PATENT DOCUMENTS

JP   57-97526   * 12/1983
JP   2-120710   * 12/1992

OTHER PUBLICATIONS

Trypsin Complex Ointment disclosure. Downloaded from the world wide web on Aug. 30, 2007.*
"Preparation and in vivo Characteristics of Biodegradable Copoly-(DL-alanine/ β-ethyl L-aspartate) Formlations with Various Structures of Drug Dispersion", Asano et al. Yakuzaigaku, Vol. 49, No. 2 (1989) 116-126.

* cited by examiner

*Primary Examiner*—Michael G Hartley
*Assistant Examiner*—Paul Dickinson
(74) *Attorney, Agent, or Firm*—Merchant & Gould P.C.

(57) ABSTRACT

A method for producing compression-melt molded product using polylactic acid powder is described. The method comprises the steps of: 1) heat-melting polylactic acid having a weight-average molecular weight of 3,000-40,000 at 140-220° C., 2) allowing the melted polylactic acid to cool down to solidify at an ordinary or a lower temperature, 3) pulverizing the solidified polylactic acid at an ordinary temperature into powder, and 4) compressing the powder or a mixture powder prepared by addition of another ingredient, e.g., a biologically active compound, to the carrier powder in a mold at an ordinary temperature to cause the polylactic acid to melt into a molded product of a predetermined shape.

8 Claims, 2 Drawing Sheets

DRUG-RELEASING SYSTEM OF BIODEGRADABLE POLYMER TYPE

TECHNICAL FIELD

The present invention relates to a biodegradable polymer-based drug releasing system, particularly to such a system utilizing a certain biodegradable polymer for controlled release of drugs or agricultural chemicals.

BACKGROUND ART

Systems for controlled release of biologically active compounds are known, e.g., those which contain a biologically active compound in a base of suitable biodegradable polymers such as polylactic acid or polyglycolic acid. For producing such systems, it is necessary to mix a biodegradable polymer with a biologically active compound, and then mold the mixture thus prepared into certain shapes, e.g., a rod-like, plate-like or spherical shape, etc. appropriate for respective intended ways of use. The procedures for molding the mixture into those shapes generally include either heat-melting the mixture and pouring it into a mold, followed by cooling and solidification, or dissolving the mixture in a solvent, pouring the solution into a mold, and then evaporating the solvent. However, high temperatures are required for heat-melting, i.e., 140-175° C. for DL-polylactic acid or polylactic acid/polyglycolic acid, and 190-220° C. for D- or L-polylactic acid. Many of biologically active compounds cannot withstand such high temperatures. Therefore, a method that includes a process of heat-melting of a mixture of a biologically active compound with polylactic acid or polyglycolic acid is not suitable as a general method for preparing a drug-releasing system. Also, in a method including a process of molding polylactic acid or polylactic acid/polyglycolic acid after dissolving them in a solvent, complete removal of the solvent from the molded product becomes necessary, which in general is very difficult, rendering such a method unsuitable as a general method for preparing a drug-releasing system.

On the other hand, Japanese Patent Application Publication S61-172813 describes a composite which is prepared by mechanically mixing a biologically active compound with DL-polylactic acid having a molecular weight of 1,000-5,000 or L- or D-polylactic acid having a molecular weight of 1,000, and heat-softening the mixture at 30-50° C. under the pressure of 200 kgf/cm$^2$ (=1.96×10$^3$ N/cm$^2$). Japanese Patent Application Publication No. S62-207227 discloses a releasing system which is prepared by heat treatment of poly(DL-lactic acid) (Mn=15,000) at 40° C. for 10 seconds under the pressure of 50 kgf/cm$^2$ (=4.9×10$^2$ N/cm$^2$).

However, in the method for preparing the systems described in these publications, it is typically DL-polylactic acid that is shown to be moldable without heating, according to what is described in the examples. Examples employing one of the optical isomers, D- or L-polylactic acid, alone are disclosed but they are limited to those having a very small molecular weight (1,000). As aforementioned, the melting point of polylactic acid differs depending on whether the polylactic acid is DL-, D- or L-form, among which also the softening temperatures naturally differ. The melting and softening points vary depending on the molecular weight; the greater the molecular weight, the more difficult it becomes to soften and melt. For example, a study performed by the present inventors using powder directly prepared by pulverizing L-polylactic acid having a weight-average molecular weight of over 3,000, its compression under room temperature caused no fusion of the particles, failing to give a molded product.

Upon this background, the objective of the present invention is to provide a method for production of a drug-releasing system containing polylactic acid and a biologically active compound, wherein the method requires neither heating nor solvent in the molding of the mixture of the biologically active compound and polylactic acid.

DISCLOSURE OF INVENTION

The present inventors found that the powder obtained through a process in which polylactic acid was once heat-melted at a temperature in a predetermined range, then cooled down to solidify at an ordinary or a lower temperature, and pulverized at an ordinary temperature behaves differently under pressure from powder that was obtained by directly pulverizing polylactic acid that had not been subjected to a heat-melting process at a predetermined temperature. More specifically, while powder prepared by simple pulverization of L-polylactic acid could not be molded under pressure at an ordinary temperature, thus maintaining the powder form, powder prepared by pulverizing polylactic acid that had once been heat-melted and cooled down to solidify at an ordinary or a lower temperature, allows easy fusion of polylactic acid particles, thus, under mild pressure, giving a transparent molded product through easy melting and unification of the polylactic acid powder. Also found was that a mixture prepared by mixing such powder from heat-melted polylactic acid with other ingredients, e.g., a biologically active compound, allows melting and unification of polylactic acid under mild pressure, thus giving a molded product containing a dispersed biologically active compound. It was further found that a molded product prepared in such a manner releases a biologically active compound continuously almost without an initial burst, and at a substantially constant (zero-order) rate, as opposed to a two-phased release observed with a molded product prepared by a conventional method of compression with heating. The present invention was accomplished through further studies about various applications based on these findings.

Thus, the present invention provides a method for production of a polylactic acid-based compression-melt molded product comprising the steps of:

1) heat-melting polylactic acid having a weight-average molecular weight of 3,000-40,000 at 140-220° C., 2) allowing the melted polylactic acid to cool down to solidify at an ordinary or a lower temperature, 3) pulverizing the solidified polylactic acid at an ordinary temperature into powder, and 4) compressing the powder, or a mixture powder prepared by addition of another ingredient to the carrier powder, in a mold at an ordinary temperature to cause the polylactic acid to melt into a molded product of a predetermined shape.

The method for production may further comprise a step of producing one or more smaller-sized molded products by cutting a length of molded product prepared by the above-defined steps into shorter parts.

The present invention further provides a method for production of a biodegradable polymer-based drug releasing system comprising the steps of:

1) heat-melting polylactic acid having a weight-average molecular weight of 3,000-40,000 at 140-220° C., 2) allowing the melted polylactic acid to cool down to solidify at an ordinary or a lower temperature, 3) pulverizing the solidified polylactic acid at an ordinary temperature into powder, and 4) mixing the powder with a powder of a biologically active compound and compressing thus prepared mixture powder in a mold at an ordinary temperature to cause the polylactic acid to melt into a molded product of a predetermined shape.

The method for production may further comprise a step of producing one or more smaller-sized drug-releasing systems by cutting a length of molded system prepared by the above-defined steps into shorter parts.

Any of DL-, D- and L-polylactic acid may be employed in the present invention. In the present invention, the range of molecular weight in which particularly notable improvement of fusion of the polylactic acid particles is achieved is 8,000-30,000 for DL-polylactic acid and 3,000-30,000 for D- and L-polylactic acid.

In the present invention, the process of compression may be conducted under such pressure that will cause the polylactic acid powder to melt and unite in several to several dozen seconds.

In the present invention, in order to ensure pressure-driven melting and unification of polylactic acid to take place in the mixture of polylactic acid and another ingredient or a biologically active compound, the weight ratio of such another ingredient or a biologically active compound to polylactic acid is usually not more than 2/5, preferably not more than 3/10, and particularly preferably not more than 1/9. Insofar as these ranges of weight ratio are met, the amount of such another ingredient or a biologically active compound may be determined according to the purpose of the product.

A mold used for the molding preferably has a cylindrical inner surface, and compression of a mixture powder consisting of polylactic acid and a biologically active compound preferably takes place in the direction of the axis of the mold. The cylindrical inner surface, which is not necessarily one having a circular cross section, may have an elliptic or polygonal cross section.

The present invention further provides a method for production of a biodegradable polymer-based drug releasing system comprising the steps of:

1) heat-melting polylactic acid having a weight-average molecular weight of 3,000-40,000 at 140-220° C., 2) allowing the melted polylactic acid to cool down to solidify at an ordinary or a lower temperature, 3) pulverizing the solidified polylactic acid at an ordinary temperature into powder, and 4) compressing, at an ordinary temperature, the powder or a mixture powder prepared by mixing the powder with a powder of a biologically active compound in an amount giving a weight ratio of the latter powder to the former of not more than 2/5, preferably not more than 3/10, or particularly preferably not more than 1/9, in a mold which is removably provided with a column-like core cylinder placed along the axis of the mold, to form a molded product defining a column-like hollow region, 5) removing the core cylinder and either pouring into the hollow region a mixture powder prepared by mixing powder produced through a process in which polylactic acid having a weight-average molecular weight of 3,000-40,000 is heat-melted at 140-220° C., then cooled down to solidify at an ordinary or a lower temperature and pulverized at an ordinary temperature, and powder of a biologically active compound in an amount giving a weight ratio of the latter powder to the former of not more than 2/5, preferably not more than 3/10, or particularly preferably not more than 1/9, or inserting into the hollow region a molded product produced by compressing the mixture powder at an ordinary temperature, and 6) compressing the mixture powder, or the molded product therefrom, in the hollow region at an ordinary temperature to cause the polylactic acid in the mixture powder to melt and the mixture powder to be molded appressed against the inner wall of the hollow region, thereby obtaining a united molded product.

The step of pouring into the hollow region a mixture prepared by mixing polylactic acid and a biologically active compound, or of inserting into the hollow region a molded product produced by compressing the mixture powder at an ordinary temperature, may be conducted by any method as desired, such as the method described in Yakuzaigaku, Vol.49 (No.2):p.116-126(1989) or other publicly known methods or methods based on them.

According to the above method, a biodegradable polymer-based drug releasing system is obtained in which the core consisting of a molded mixture of a drug and polylactic acid is surrounded by an molded outer shell consisting of polylactic acid alone or of a mixture of polylactic acid and a biologically active compound. The method for production may further comprise a process of producing smaller-sized drug-releasing systems by cutting a length of molded system produced by the above-defined steps into shorter parts. In the method for production, when the outer shell contains a biologically active compound, the weight ratio of the biologically active compound to polylactic acid in either the outer shell or the core may be chosen within the above-mentioned ranges, in accordance with the an intended releasing pattern. The core and the outer shell may contain the same biologically active compound or different ones.

The present invention further provides a method for production of the aforementioned biodegradable polymer-based drug releasing system consisting of a core and an outer shell, the method further comprising the steps of:

1) pouring in the mold onto the end face of the molded product with the exposed hollow region produced by the steps 1-6 above, powder produced by a process in which polylactic acid having a weight-average molecular weight of 3,000-40,000 is heat-melted at 140-220° C., then cooled down to solidify at an ordinary or a lower temperature and pulverized at an ordinary temperature or a mixture powder prepared by mixing said powder and powder of a biologically active compound in an amount giving a weight ratio of the latter powder to the former of not more than 2/5, preferably not more than 3/10, or particularly preferably not more than 1/9, and 2) compressing said powder or the mixture powder in the direction of the axis of the mold at an ordinary temperature to cause the polylactic acid to melt, thereby molding the polylactic acid powder or the mixture powder, thus giving one united molded product together with the molded product produced by the steps 1-6.

According to the method for production, a biodegradable polymer-based drug releasing system is obtained which has also an outer shell covering the exposed hollow region, whose interior has been completely or partially filled with a molded product consisting of a mixture of polylactic acid and a biologically active compound. In the method for production, where covering the exposed hollow region with a mixture of polylactic acid and a biologically active compound, the weight ratio of the biologically active compound to polylactic acid in the mixture is usually not more than 2/5, preferably not more than 3/10, and particularly preferably not more than 1/9. The weight ratio may be adjusted to the weight ratio of the biologically active compound contained in the already formed outer shell, though such an adjustment is not necessary. The core and the outer shell may contain the same or different biologically active compounds.

The present invention further provides a method for production of a biodegradable polymer-based drug-releasing system comprising the steps of:

1) heat-melting polylactic acid having a weight-average molecular weight of 3,000-40,000 at 140-220° C., 2) allowing the melted polylactic acid to cool down to solidify at an ordinary or a lower temperature, 3) pulverizing the solidified polylactic acid at an ordinary temperature into powder, and 4) compressing, at an ordinary temperature, the powder or a mixture powder prepared by mixing the powder with a powder of a biologically active compound in an amount giving a weight ratio of the latter powder to the former of not more than 2/5, preferably not more than 3/10, or particularly preferably not more than 1/9, in a mold which is removably provided with a column-like core cylinder placed along the axis of the mold to form a molded product defining a column-like hollow region, 5) removing the core cylinder and pouring into the hollow region a biologically active compound or a composition containing the same, 6) pouring onto the end face of the molded product with the exposed hollow region, powder produced by a process in which polylactic acid having a weight-average molecular weight of 3,000-40,000 is heat-melted at 140-220° C., then cooled down to solidify at an ordinary or a lower temperature and pulverized at an ordinary temperature or a mixture powder prepared by mixing said powder and powder of a biologically active compound in an amount giving a weight ratio of the latter powder to the former of not more than 2/5, preferably not more than 3/10, or particularly preferably not more than 1/9, and 7) compressing said powder or the mixture powder in the direction of the axis of the mold at an ordinary temperature to cause the polylactic acid to melt, thereby molding the polylactic acid powder or the mixture powder, thus giving one united molded product containing in the hermetically sealed hollow region a biologically active compound or a composition thereof.

According to the method for production, a biodegradable polymer-based drug releasing system is obtained in which a biologically active compound or a composition thereof is covered by an outer shell made of polylactic acid or a mixture consisting of polylactic acid and a biologically active compound. The biodegradable polymer-based drug releasing system obtained according to the production method can contain in its interior a biologically active compound in its pure form or at high concentrations. The biologically active compound contained in the outer shell may be the same as or different from the biologically active compound contained in the interior.

Also in the production of the aforementioned biodegradable polymer-based drug releasing system having a structure consisting of an outer shell and a core, any of DL-, D- and L-polylactic acid may be used. In the method for production, the molecular weight range within which most remarkable benefit is obtained is 8,000-30,000 for DL-polylactic acid and 3,000-30,000 for D- or L-polylactic acid.

Also in the production of the aforementioned biodegradable polymer-based drug releasing system consisting of an outer shell and a core, a compression process may be usually conducted under such a pressure that causes polylactic acid powder to melt and become united.

Any compound may be employed as desired as another ingredient or a biologically active compound in the aforementioned compression-melt molded product from polylactic acid or in any of the aforementioned biodegradable polymer-based drug-releasing systems. Examples of such compounds included, but are not limited to, antibiotics, antimicrobials, antivirals, vascularization suppressors, anti-glaucoma agents, anti-cataract agents, anticancer agents, vaccine antigens and physiologically active peptides.

The present invention also provides compression-melt molded products from polylactic acid or biodegradable polymer-based drug-releasing systems of that are produced by any of the aforementioned production methods. Such systems may be implanted in various parts of the body according to the purpose of application, e.g., beneath the skin, in the eyeball, in the brain, or the like.

BEST MODE FOR CARRYING OUT THE INVENTION

Figure 1:
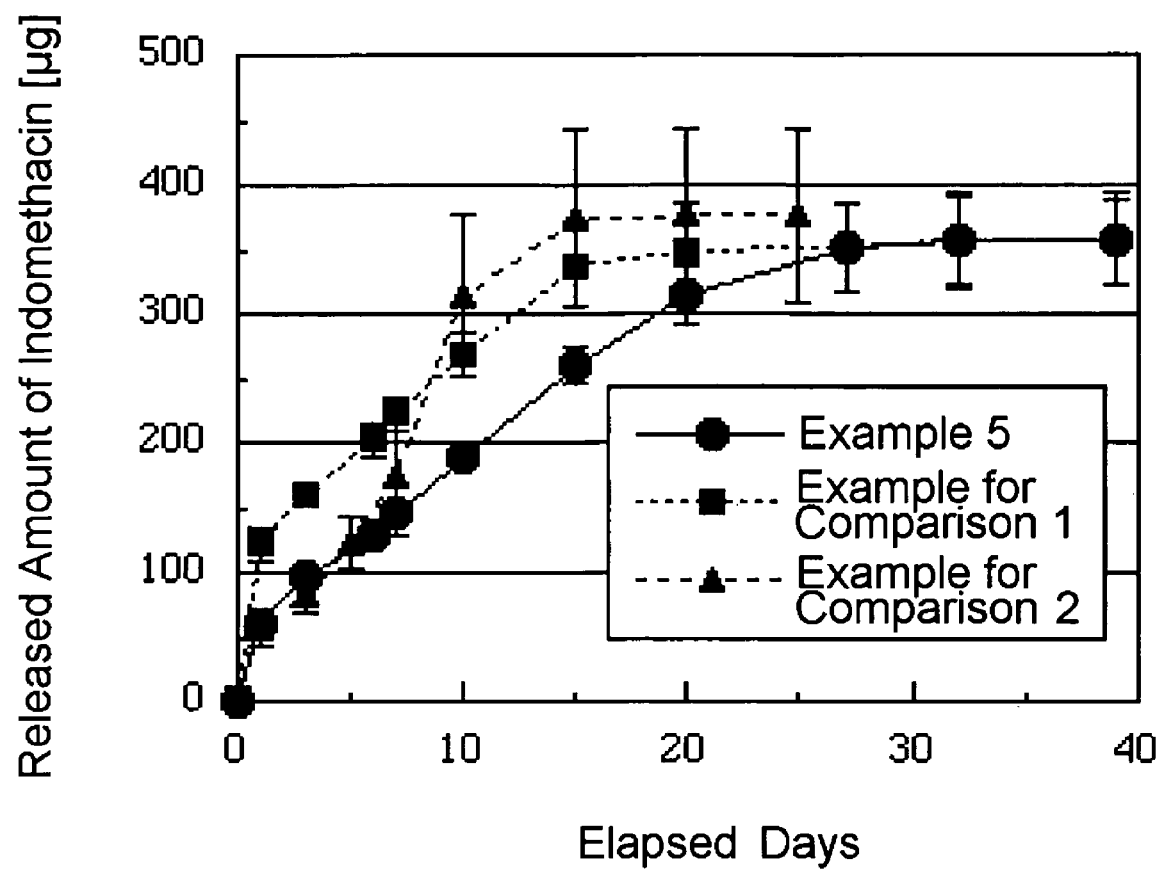
FIG. 1 is a graph illustrating the amount of indomethacin released over time from the drug-releasing systems of Example 5 and Examples for Comparison 1 and 2.

In the present invention, the term an "ordinary temperature" means a temperature of 20-30° C. A temperature lower than this is meant by the term a "lower temperature".

A biologically active compound and polylactic acid power are mixed at an ordinary temperature. However, if a biologically active compound is a liquid at an ordinary temperature, they may be mixed at a lower temperature in order to allow the compound to solidify during the mixing process.

The present invention has enabled complete melting and unification of polylactic acid particles under a small pressure as a result of providing the steps of heat-melting and cooling down for solidification of polylactic acid before pulverization and then conducting pulverization of polylactic acid at an ordinary temperature, not a lower temperature. Thus, as the present invention does not require any heating during molding, it is suitable for the production of a biodegradable polymer-based drug releasing system employing a biologically active compound that is sensitive to heat. Also, as only a small pressure is required to cause polylactic acid particles to melt in the present invention, it is also suitable when employing a biologically active compound that is sensitive to pressure. Further, as the present invention needs no solvent in molding polylactic acid, it has advantages that no solvent removal process is required, and that a safer product is obtained than by a method for production utilizing a solvent.

Among the biodegradable polymer-based drug-releasing systems produced according to the present invention, those of the simplest structure can be used to release a biologically active compound continuously and at a nearly constant rate for a prolonged time.

Among the biodegradable polymer-based drug releasing system produced according to the present invention, those consisting of a core and an outer shell can be used to release a biologically active compound in different releasing patterns through proper setting of the relative dimensions of the core and the outer shell as well as the weight ratio of the biologically effective compound contained in the core and the outer shell, and also in accordance with whether the end face of the core is exposed or it is covered with a shell consisting of, or comprising, polylactic acid. For example, systems which have an outer shell made of neat polylactic acid and whose exposed core in the end face is also covered with the shell can be used to continuously release a biologically active compound at a constant rate only after the lapse of certain length of time during which no release of the biologically active compound takes place, rendering them to be useful for medical applications such as vaccine inoculation, or in the field of agriculture (e.g. for poultry plants), and the like. Using a system containing a biologically active compound also in the outer shell, it is possible to realize release of a biologically active compound at one constant rate until the lapse of a certain period of time and then, after the lapse of the period, at another constant rate. Furthermore, by employing a multilayered core/outer shell, the present invention can readily provide a system that releases a biologically active compound in a pulsed pattern. For providing a multilayered core/outer shell, the step of core formation, for example but without limitation, may include a further step, in which a second, narrower core cylinder is employed to define a narrower hollow region in the core, and a mixture of polylactic acid and a biologically active compound is compressed in the hollow region to melt and become united.

If different biologically active compounds are used in the outer shell and the core, respectively, a biodegradable polymer-based drug releasing system will be obtained which continuously releases the drug contained in the shell at a constant rate until the lapse of a predetermined period of time, and then, after the lapse of the period, continuously releases the drug contained in the core at a constant rate. Also, in the case of a biodegradable polymer-based drug releasing system in which the core is exposed in the end face of the system, addition of different biologically active compound in the shell and the core, respectively, gives a drug-releasing system which continuously releases the both biologically active compounds at the same time and at constant rates, avoiding direct contact of the both compounds. This method is useful, particularly where, e.g., the both biologically active compounds are chemically destabilized by their direct contact.

Furthermore, a biodegradable polymer-based drug releasing system can be provided in which a biologically active compound or a composition thereof is encapsulated in a shell consisting of polylactic acid or a mixture of polylactic acid and a biologically active compound, in order to release a biologically active compound at a burst only after the lapse of a certain period of time during which the biologically active compound is not released. Using a system of this type, the content of a biologically active compound can be increased without difficulty, as the such a system can contain a pure biologically active compound or a composition containing a high concentration of the compound.

In the present invention, a compression-melt molded product or a biodegradable polymer-based drug releasing system may be provided in any of a variety of shapes as desired, e.g., a rod-like, plate-like, spherical shapes, etc. in accordance with the purpose of use, and the shape and structure of a mold may be determined in conformity to the intended shape of a product. In addition, by defining a through-bore or an indentation in a rod-shaped or spherical system, etc., a system of the present invention may be provided that can be attached to another support body such as a supporting element of intraocular lens.

The present invention will be described in further detail with reference to Examples. However, it is not intended that the present invention be restricted to the Examples.

Example 1

L-polylactic acid having a weight-average molecular weight of 5,000 was heated to melt at 150° C., then allowed to cool down to solidify, and pulverized in a mortar at an ordinary temperature. The powder of pulverized L-polylactic acid was poured into a Teflon tube of approx. 1-mm inside diameter. Stainless steel rods of approx. 1-mm diameter were inserted from both end of the tube and the L-polylactic acid was gently pressed for several to several dozen seconds at room temperature. This cause the powder of polylactic acid to melt and become united into a transparent rod of L-polylactic acid (1 mm in diameter, 3 mm in length).

Example 2

A Teflon rod of 1-mm diameter and 2 cm in length was inserted into a Teflon tube of 2-mm inside diameter along the central axis thereof. The both end of the Teflon tube were plugged with spacer tubes (of Teflon) of 1-mm inside diameter and 2-mm outside diameter, with the Teflon rod protruding from both ends of the Teflon tube inserted in the spacer tubes, thereby enabling to secure the Teflon rod along the central axis of the Teflon tube of 2-mm inside diameter. One of the spacers was removed, the same polylactic acid powder as used in Example 1 was poured into the space defined by the Teflon tube and the Teflon rod, and the spacer that had been removed was attached again. The polylactic acid powder was gently pressed from both ends using the spacers placed on both ends for several to several dozen seconds at room temperature to cause polylactic acid powder to melt and become united, thereby forming a transparent molded product of L-polylactic acid having a passing through hollow region. Only the Teflon rod used as a core cylinder was then removed, a mixture powder consisting of the polylactic acid powder used in Example 1 and indomethacin (polylactic acid:indomethacin=9:1 (by weight)) was poured into the hollow region of the molded product of polylactic acid, and gently pressed from both ends using stainless steel rods of 1-mm diameter for several to several dozen seconds at room temperature, causing the mixture powder to solidify. The product comprising a core, which consists of polylactic acid and the drug, and surrounding polylactic acid was removed and cut into 3 mm in length.

Example 3

A molded produced of 2-mm outer diameter and 3 mm in length prepared in Example 2 was inserted into a Teflon tube of 2-mm inside diameter. On both ends of the molded product was poured the same polylactic acid powder as used in Example 1, and the powder was gently pressed with stainless steel rods of 2-mm diameter for several to several dozen seconds at room temperature to cause the polylactic acid powder to melt and become united, giving a molded product.

Example 4

A Teflon rod of 1-mm diameter and 2 cm in length was inserted into a Teflon tube of 2-mm inside diameter along the central axis thereof. The both end of the Teflon tube were plugged with spacer tubes (of Teflon) of 1-mm inside diameter and 2-mm outside diameter, with the Teflon rod protruding from both ends of the Teflon tube inserted in the spacer tubes, thereby securing the Teflon rod along the central axis of the Teflon tube of 2-mm inside diameter. One of the spacers was removed, the same polylactic acid powder as used in Example 1 was poured into the space defined by the Teflon tube and the Teflon rod, and the spacer that had been removed was attached again. The polylactic acid powder was gently pressed using the spacers for several to several dozen seconds at room temperature to cause polylactic acid powder to melt and become united, thereby forming a transparent molded product of L-polylactic acid having a passing through hollow region. Only the Teflon rod used as a core cylinder was then removed. Indomethacin powder was poured into the hollow region of the molded product of polylactic acid, and the same polylactic acid powder as used in Example 1 then was poured on both ends of the molded product and gently pressed with stainless steel rods of 2-mm diameter for several to several dozen seconds at room temperature to cause the polylactic acid powder to melt, thereby giving a united molded product encasing indomethacin in the hollow region thereof.

Example 5

Nine hundred mg of L-polylactic acid having a weight-average molecular weight of 5,000 was heated to melt at 180° C., then allowed to cool down for one minute to solidify, and pulverized in a mortar for five minutes at an ordinary temperature. The polylactic acid powder thus obtained was mixed with indomethacin at a weight ratio of 9:1. The mixture powder was poured into a Teflon tube of approx. 1-mm inside diameter up to a height of approx. 1 cm. Stainless steel rods of approx. 1-mm diameter were inserted from both ends of the tube and the polylactic acid powder was gently pressed for several to several dozen seconds at an ordinary temperature to cause the polylactic acid powder to melt and integrate into a polylactic acid rod (1 mm in diameter, 3 mm in length) containing indomethacin. The rod was placed in five ml of phosphate buffer (pH 7), and stirred by shaking for 36 days at 37° C. at 180 cpm. During the stirring period, the whole volume of the fluid was exchanged over time, and indomethacin concentration in the solution determined by HPLC to calculate the amount of indomethacin released into the solution. The results are shown in FIG. 1 as the cumulative amount of released indomethacin. As apparent from FIG. 1, it is noted that indomethacin was released at a substantially constant rate (zero-order), substantially without an initial burst, for 20 days up to its almost complete release.

Example 6

Nine hundred mg of L-polylactic acid having a weight-average molecular weight of 5,000 was heated to melt at 180° C., then allowed to cool down for one minute to solidify, and pulverized in a mortar for five minutes at an ordinary temperature. The polylactic acid powder thus obtained was mixed with indomethacin at a weight ratio of 10:3. The mixture powder was poured into a Teflon tube of approx. 1-mm inside diameter up to a height of approx. 1 cm. Stainless steel rods of approx. 1-mm diameter were inserted from both ends of the tube and the polylactic acid powder was gently pressed for several to several dozen seconds at an ordinary temperature to cause the polylactic acid powder to melt and integrate into a polylactic acid rod (1 mm in diameter, 3 mm in length) containing indomethacin.

Example 7

Nine hundred mg of L-polylactic acid having a weight-average molecular weight of 5,000 was heated to melt at 180° C., then allowed to cool down for one minute to solidify, and pulverized in a mortar for five minutes at an ordinary temperature. The polylactic acid powder thus obtained was mixed with indomethacin at a weight ratio of 5:2. The mixture powder was poured into a Teflon tube of approx. 1-mm inside diameter up to a height of approx. 1 cm. Stainless steel rods of approx. 1-mm diameter were inserted from both ends of the tube and the polylactic acid powder was gently pressed for several to several dozen seconds at an ordinary temperature to cause the polylactic acid powder to melt and become united into a polylactic acid rod (1 mm in diameter, 3 mm in length) containing indomethacin.

Example for Comparison 1

Nine hundred mg of L-polylactic acid having a weight-average molecular weight of 5,000 was pulverized in a mortar for five minutes at an ordinary temperature. The polylactic acid powder thus obtained was mixed with indomethacin at a weight ratio of 9:1, transferred into a petri dish and completely melted at 170-180° C. After cooling down and solidification, the mixture was pulverized in a mortar for five minutes at an ordinary temperature. The mixture powder was poured into a Teflon tube of approx. 1-mm inside diameter up to a height of approx. 1 cm. Stainless steel rods of approx. 1-mm diameter were inserted from both ends of the tube and the mixture powder was compression molded at an ordinary temperature to form a polylactic acid rod (1 mm in diameter, 3 mm in length) containing indomethacin. The rod was placed in five ml of phosphate buffer (pH 7), and stirred by shaking for 36 days at 37° C. at 180 cpm. During the stirring period, the whole volume of the fluid was exchanged over time, and indomethacin concentration in the solution determined by HPLC to calculate the amount of indomethacin released into the solution. The results are shown in FIG. 1 as the cumulative amount of released indomethacin. As apparent from FIG. 1, it is noted that the release of indomethacin from this rod of this Example for Comparison exhibits an initial burst.

Example for Comparison 2

Nine hundred mg of L-polylactic acid having an average molecular weight of 5,000 was pulverized in a mortar for five minutes at an ordinary temperature. The polylactic acid powder thus obtained was mixed with indomethacin at a weight ratio of 9:1, and poured into a Teflon tube up to a height of approx. 1 cm. Stainless steel rods of approx. 1-mm diameter were inserted from both end of the tube and compression-molding was conducted while heat-softening at 80-100° C. to form a polylactic acid rod (1 mm in diameter, 3 mm in length) containing indomethacin. The rod was placed in five ml of phosphate buffer (pH 7), and stirred by shaking for 25 days at 37° C. at 180 cpm. During the stirring period, the whole volume of the fluid was exchanged over time, and indomethacin concentration in the solution determined by HPLC to calculate the amount of indomethacin released into the solution. The results are shown in FIG. 1 as the cumulative amount of released indomethacin. As apparent from FIG. 1, it is noted that the release of indomethacin from this rod of this Example for Comparison exhibited a typical two-phased pattern having bursts at initial and late stages.

Example of Implantation Test

Releasing Characteristics of Intraocular Biodegradable Implantable Polymer Rod in Rabbit's Vitreous Humor Test Preparation: The indomethacin-containing polylactic acid rods of Example 5 and Examples for Comparison 1 and 2 were used.

Test Animals: Japanese albino rabbits (body weight of 1.8-2 kg), devided into three groups, were used.

Test procedure: The rabbits were given general anesthesia, and a test preparation was implanted at the center of the vitreous body, using a needle for syringe of 1-mm inside diameter, through the sclera at a site three mm away from the limbus. The rabbits were sequentially sacrificed 1, 3, 7, 14, 21, 28 and 35 days after implantation, and the eyes were removed and frozen at −80° C. The implanted preparation was separated and the content of the drug in the preparation was determined by HPLC.

Figure 2:
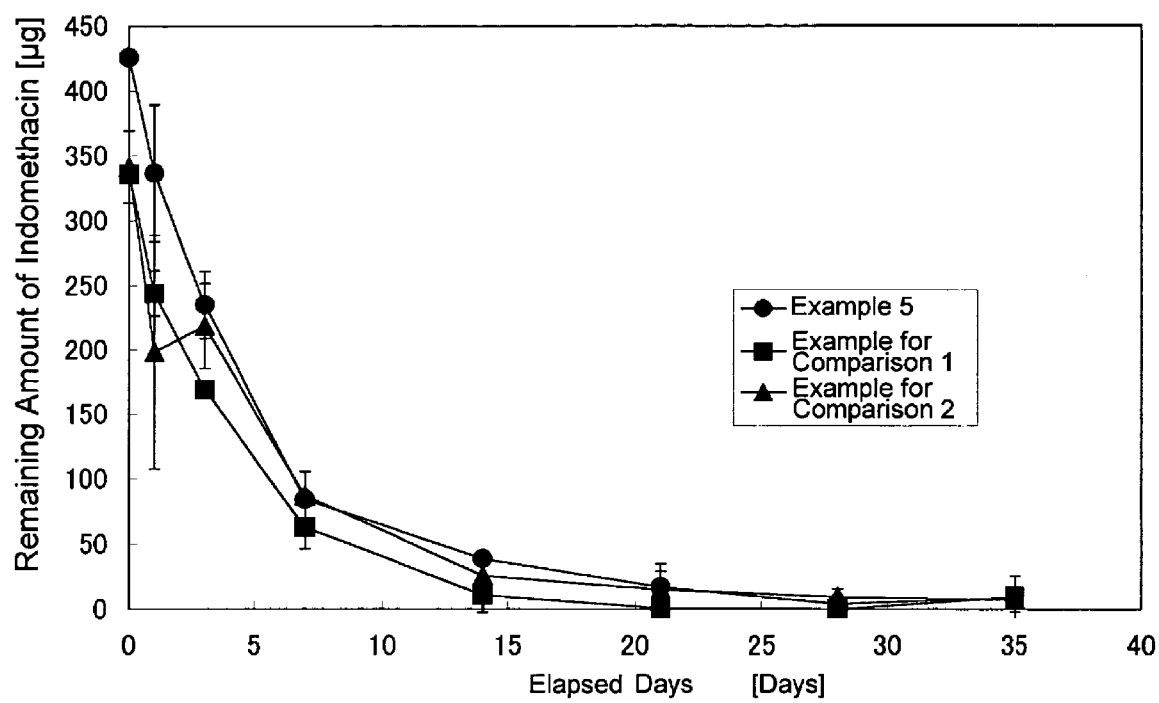
FIG. 2 is a graph illustrating the amount of indomethacin released over time from the drug-releasing systems of Example 5 and Examples for Comparison 1 and 2 implanted at the center of the vitreous body of rabbits.

Results: The results are shown by a graph in FIG. 2. The content of indomethacin in the preparation of Example 5 was found to gradually decrease over about 20 days until most of the drug was lost, indicating that the drug was constantly released from the preparation during the period. On the other hand, in the preparation of Example for Comparison 2, the content of indomethacin quickly decreased following implantation of the preparation, but remained substantially unchanged during the following period of from one through three days, and then started to decrease again. Thus, it is seen that release of indomethacin from the preparation of Example for Comparison 2 exhibited the typical 2-phased releasing pattern, i.e., a quick release immediately after implantation, a halt thereafter, followed by resumption of release. As for the preparation of Example for Comparison 1, all the indomethacin was substantially released 14 days after implantation, apparently indicating a quicker release than that of the preparation of Example 5. These findings indicate that the initial burst found in the release test in the phosphate buffer is also likely to take place with the preparations of the Examples for Comparison when they are implanted in the vitreous.

INDUSTRIAL APPLICABILITY

The present invention is particularly suited for production of a biologically degradable polymer-based drug-releasing system employing a biologically active compound that is sensitive to heat or pressure, for the present invention enables to easily and completely melt and unite polylactic acid particles by applying small pressure, thereby totally eliminating the necessity of heating during molding. Also, as no solvent is employed in the molding of polylactic acid, the present invention eliminates concern about remaining solvent in the final product.

The invention claimed is:

1. A method for production of a biodegradable polymer-based drug releasing system consisting of the steps of:
   1) heat-melting polylactic acid having a weight-average molecular weight of 3,000-40,000 at 140-220° C.,
   2) allowing the melted polylactic acid prepared in step (1) to cool down to solidify at a temperature of about 20° C. to 30° C.,
   3) pulverizing the solidified polylactic acid prepared in step (2) into powder at about 20° C. to 30° C., and
   4) mixing the powder prepared in step (3) with a powder of a biologically active compound at about 20° C. to 30° C. and compressing thus prepared mixture powder in a mold at about 20° C. to 30° C. to cause the polylactic acid to melt into a molded product of a predetermined shape.

2. The method of claim 1, wherein the polylactic acid is DL-polylactic acid, D-polylactic acid or L-polylactic acid.

3. The method of claim 1, wherein the polylactic acid is DL-polylactic acid and the weight-average molecular weight of the polylactic acid is 8,000-30,000.

4. The method of claim 1, wherein the polylactic acid is D-polylactic acid or L-polylactic acid and the weight-average molecular weight of the polylactic acid is 3,000-30,000.

5. The method of claim 1, wherein the weight ratio of the biologically active compound to polylactic acid is not more than 2:5 in the mixture powder.

6. The method of claim 1, wherein the mold has a cylindrical inner surface and the mixture powder is compressed in the direction of the axis of the mold.

7. The method of claim 1, wherein the biologically active compound is selected from the group consisting of antibiotics, antimicrobials, antivirals, vascularization suppressors, anti-glaucoma agents, anti-cataract agents, anticancer agents and vaccine antigens.

8. The method of claim 1, wherein the biologically active compound is a physiologically active peptide.

\* \* \* \* \*